(12) United States Patent
Shinayama et al.

(10) Patent No.: US 12,285,651 B2
(45) Date of Patent: Apr. 29, 2025

(54) RECOMMENDED RUNNING PACE CALCULATION SYSTEM AND RECOMMENDED RUNNING PACE CALCULATION METHOD

(71) Applicant: ASICS CORPORATION, Kobe (JP)

(72) Inventors: Ryota Shinayama, Kobe (JP); Yasuhiro Nomura, Kobe (JP); Takehiro Tagawa, Kobe (JP); Hiroto Mori, Kobe (JP); Nao Hirakawa, Kobe (JP)

(73) Assignee: ASICS CORPORATION, Kobe (JP)

( * ) Notice: Subject to any disclaimer, the term of this patent is extended or adjusted under 35 U.S.C. 154(b) by 782 days.

(21) Appl. No.: 17/055,456

(22) PCT Filed: Nov. 1, 2019

(86) PCT No.: PCT/JP2019/043166
§ 371 (c)(1),
(2) Date: Nov. 13, 2020

(87) PCT Pub. No.: WO2021/084762
PCT Pub. Date: May 6, 2021

(65) Prior Publication Data
US 2021/0362006 A1    Nov. 25, 2021

(51) Int. Cl.
*A63B 24/00*    (2006.01)
*A63B 69/00*    (2006.01)
*A63B 71/06*    (2006.01)

(52) U.S. Cl.
CPC ...... *A63B 24/0062* (2013.01); *A63B 24/0006* (2013.01); *A63B 24/0075* (2013.01); *A63B 69/0028* (2013.01); *A63B 71/06* (2013.01)

(58) Field of Classification Search
CPC ............ A63B 24/0075; A63B 69/0028; A63B 24/0062; A63B 24/0006; A63B 71/06; G16H 20/30; G06F 17/18
See application file for complete search history.

(56) References Cited

U.S. PATENT DOCUMENTS

| | | |
|---|---|---|
| 8,784,115 B1 | 7/2014 | Chuang |
| 9,724,565 B2 | 8/2017 | Hoffman et al. |
| 2019/0266505 A1 | 8/2019 | Gindre et al. |

FOREIGN PATENT DOCUMENTS

| | | |
|---|---|---|
| JP | H09178869 A | 7/1997 |
| JP | 2009236683 A | 10/2009 |
| JP | 2015161602 A | 9/2015 |

OTHER PUBLICATIONS

International Search Report; Written Opinion; and Notification of Transmittal of the International Search Report and the Written Opinion of the International Searching Authority, or the Declaration issued in PCT/JP2019/043166; mailed Dec. 17, 2019.

(Continued)

*Primary Examiner* — Lisa M Caputo
*Assistant Examiner* — Cynthia L Davis
(74) *Attorney, Agent, or Firm* — Studebaker Brackett PLLC (57) ABSTRACT

A recommended running pace calculation system and the like capable of calculating a recommended running pace that is recommended to a runner to be evaluated in a distance running. A recommended running pace calculation system according to the present invention includes a correlation storage device in which a first correlation is stored, the first correlation including correlations between running distances run by unspecified runners and their fastest running paces, a running pace acquisition device configured to acquire running paces for predetermined sections in a distance running run by a runner to be evaluated, the distance running having (Continued)

a predetermined length, a correction device configured to extract a fastest running pace of the running paces of the runner to be evaluated for the predetermined sections, and a recommended running pace calculation device configured to calculate a recommended running pace.

4 Claims, 8 Drawing Sheets

(56)  References Cited

OTHER PUBLICATIONS

The extended European search report issued by the European Patent Office on Jan. 5, 2022, which corresponds to European Patent Application No. 19927568.6-1222 and is related to U.S. Appl. No. 17/055,456.

RECOMMENDED RUNNING PACE CALCULATION SYSTEM AND RECOMMENDED RUNNING PACE CALCULATION METHOD

TECHNICAL FIELD

The present invention relates to a recommended running pace calculation system and a recommended running pace calculation method that calculate a recommended running pace in a distance running having a predetermined length such as a full marathon. In particular, the present invention relates to a recommended running pace calculation system and a recommended running pace calculation method that are capable of calculating, based on running paces in a distance running that are acquired through an actual run of a runner to be evaluated, a recommended running pace in the distance running that is recommended to the runner to be evaluated.

BACKGROUND ART

In a long-distance running such as a full marathon and a half marathon, it is often the case that a runner slows down from the middle stage into the latter half of the run due to running the former half of the run at a running pace faster than that commensurate with an ability of the runner. Ideally, a runner runs a long-distance running at a constant running pace from the beginning to the end. It is considered that a runner who slows down can make a better record if the runner runs at a constant running pace commensurate with an ability of the runner. Accordingly, there is a demand for calculating a constant running pace commensurate with an ability of each runner as a recommended running pace.

Here, Patent Literature 1 presents an apparatus that predicts a running time of a long-distance running such as a full marathon from a running time of a distance shorter than that of the long-distance running.

Specifically, the apparatus described in Patent Literature 1 is made to solve a problem of a runner unable to know at all how much time the runner can reduce in an actual long-distance running such as a full marathon until the runner actually runs the long-distance running even though the runner can grasp improvement in an ability of the runner in a daily running training of a short distance when a running time of the distance is reduced (Paragraph [0003] of Patent Literature 1).

To solve the problem, the apparatus described in Patent Literature 1 is configured to statistically acquire running time data (mathematical data) in which running times (best times) for a distance of 5 km or 10 km, which is a reference running distance, are associated with predicted running times of a full marathon, store the running time data, and based on the mathematical data, calculate, from a best time of a runner to be evaluated for the reference running distance, a predicted running time of the runner to be evaluated for a full marathon, target lap times for sections, and the like (Claims, Paragraph [0020], Abstract, etc. of Patent Literature 1).

With the apparatus described in Patent Literature 1, a predicted running time of a long-distance running such as a full marathon based on a best time of a runner to be evaluated for a distance of 5 km or 10 km. Furthermore, it is considered that, by dividing the calculated predicted running time by a distance that is run in a long-distance running to calculate an average running pace, the resultant average running pace can be calculated as a recommended running pace that is recommended to a runner to be evaluated.

However, the apparatus described in Patent Literature 1 has a problem in that the device is inconvenient because it is necessary for the runner to be evaluated to actually run at full speed for a distance of 5 km or 10 km, which is shorter than the long-distance running such as a full marathon, to measure a running time of the run so as to calculate the recommended running pace in the long-distance running.

CITATION LIST

Patent Literature

[Patent Literature 1] JP9-178869A

SUMMARY OF INVENTION

Technical Problem

An objective of the present invention, which has been made to solve the problems of the related art described above, is to provide a recommended running pace calculation system and a recommended running pace calculation method that are capable of calculating, based on running paces in a distance running having a predetermined length such as a full marathon that are acquired through an actual run of a runner to be evaluated, a recommended running pace in the same distance running that is recommended to the runner to be evaluated.

Solution to Problem

To solve the problem, the present inventors conducted intensive studies, and as a result, the present inventors paid attention to treating a fastest running pace of running paces for predetermined sections in a distance running that is acquired through an actual run by a runner to be evaluated as a running pace that is commensurate with an intrinsic ability of the runner to be evaluated. Based on the attention, the present inventors conceived that correlations between running distances run by unspecified runners and their fastest running paces are acquired, for example, in a statistical manner, and running paces for predetermined sections in a distance running that are acquired through an actual run by a runner to be evaluated are corrected based on a fastest running pace of these running paces and the correlations. Then present inventors found that using the corrected running paces for the predetermined sections enables a recommended running pace that is appropriate for the runner to be evaluated in the same distance running to be obtained.

The present invention is completed based on findings made by the present inventors described above.

That is, to solve the problem, the present invention provides, as a first aspect, a recommended running pace calculation system comprising: a correlation storage device in which a first correlation is stored, the first correlation including correlations between running distances run by unspecified runners and fastest running paces of the unspecified runners; a running pace acquisition device configured to acquire running paces for predetermined sections in a distance running run by a runner to be evaluated, the distance running having a predetermined length; a correction device configured to extract a fastest running pace of the running paces of the runner to be evaluated for the predetermined sections acquired by the running pace acquisition device, and to correct the running paces of the runner to be evaluated for the predetermined sections acquired by the running pace acquisition device, based on the extracted fastest running pace and the first correlation stored in the correlation storage device; and a recommended running pace calculation device configured to calculate a recommended running pace in the distance running recommended to the runner to be evaluated based on the corrected running paces of the runner to be evaluated for the predetermined sections corrected by the correction device.

According to the first aspect of the present invention, the running pace acquisition device acquires running paces for predetermined sections in a distance running having a predetermined length that is actually run by a runner to be evaluated. Then, the correction device extracts a fastest running pace of the running paces of the runner to be evaluated for the predetermined sections, and based on the extracted fastest running pace and the first correlation (including correlations between running distances run by unspecified runners and their fastest running paces) stored in the correlation storage device, the correction device corrects the running paces of the runner to be evaluated for the predetermined sections. The corrected running paces for the predetermined sections are running paces for the predetermined sections that are commensurate with the fastest running pace of the runner to be evaluated, in other words, an intrinsic ability of the runner to be evaluated. Then, the recommended running pace calculation device calculates a recommended running pace in the same distance running recommended to the runner to be evaluated based on the corrected running paces of the runner to be evaluated for the predetermined sections. The recommended running pace can be calculated in a form of, for example, an average value of the corrected running paces for the predetermined sections. According to the findings made by the present inventors, the calculated recommended running pace is a recommended running pace appropriate to the runner to be evaluated.

As seen from the above, according to the first aspect of the present invention, a recommended running pace that is recommended to a runner to be evaluated for a distance running can be calculated based on running paces in the same distance running (the running paces for the predetermined sections) that are acquired through an actual run of the runner to be evaluated.

Note that the first correlation can be created statistically by measuring running paces that are obtained by dividing times taken by unspecified runners to run various running distances at highest speeds by the running distances, and by associating and organizing correlations between the running distances and the running paces, as with the apparatus described in Patent Literature 1 and the like, for example.

The first correlation shows correlations between running distances and fastest running paces, in a table form or a function form, such as those who can run 5 km at a fastest running pace of 260 sec/km can run 10 km at a fastest running pace of 270 sec/km, and those who can run a half marathon at a fastest running pace of 280 sec/km can run a full marathon at a fastest running pace of 310 sec/km.

Specifically, in the first aspect of the present invention, it is preferred that in the correlation storage device, a correction function corresponding to a fastest running pace created based on the first correlation, is stored, and the correction device corrects the running paces of the runner to be evaluated for the predetermined sections based on the extracted fastest running pace of the runner to be evaluated and the correction function.

In the first aspect of the present invention, it is preferred that the correction function is created by: a first step of calculating, using the first correlation, an ideal average running pace in the distance running, on an assumption that a given section is run at a fastest running pace and a remaining section is walked; and a second step of determining the correction function such that the ideal average running pace calculated in the first step is obtained in a case where the running paces for the predetermined sections in the distance running with the assumption are corrected based on the correction function corresponding to the fastest running pace.

With the preferred configuration described above, in the first step, an ideal average running pace in a distance running, on an assumption that a given section (e.g., a first section in the distance running) is run at a fastest running pace and a remaining section is walked, is calculated using the first correlation. Specifically, in a case where a runner runs the given section (a distance) at a fastest running pace, using the first correlation enables calculation of at what running pace the runner runs a distance running if the runner who can run the given section at the fastest running pace runs the distance running at full speed. For example, using the first correlation enables calculation such that a runner who can run some 10 km at a running pace of 270 sec/km can run a full marathon at a running pace of 310 sec/km if the runner runs the full marathon at full speed. Then, in the first step, the running pace calculated using the first correlation is determined as the ideal average running pace in the distance running, on an assumption that the given section is run at the fastest running pace and the remaining section is walked.

Next, with the preferable configuration described above, in the second step, the correction function is determined such that the ideal average running pace calculated in the first step is obtained in a case where the running paces for the predetermined sections in the distance running with the assumption (the distance running on the assumption that the given section is run at the fastest running pace and the remaining section is walked) are corrected based on the correction function corresponding to the fastest running pace. Specifically, the correction function is determined such that, in a case where an average running pace of the distance running with the assumption is calculated using the corrected running paces for the predetermined sections, the calculated average running pace matches the ideal average running pace calculated in the first step.

The correction function corresponding to the fastest running pace is to be obtained by performing the first step and the second step described above while varying the fastest running pace in the given section in the distance running with the assumption to various values.

Note that the correction function determined by the preferred configuration described above is determined based on the distance running with the assumption and can be used also for a distance running that is actually run by a runner to be evaluated, according to the findings made by the present inventors. That is, even when the correction function determined by the preferred configuration described above is used to correct running paces for predetermined sections in the distance running that is actually run by the runner to be evaluated, a recommended running pace that is appropriate for the runner to be evaluated can be calculated.

In the first aspect of the present invention, it is preferred that the correction function is expressed as a function of a fastest running pace and running pace for each predetermined section of the distance running as variables.

The correction function can be obtained, for example, by performing the first step and the second step in the preferred configuration described above while varying the fastest running pace in the given section and a running pace for a section walked in the distance running with the assumption to various values.

In the first aspect of the present invention, it is preferred that with Li denoting lengths of predetermined sections i (i=1 to n) in the distance running run by the runner to be evaluated, Pi denoting running paces for the predetermined sections i, and Pmax denoting a fastest running pace of the running paces Pi for the predetermined sections i, the correction device corrects the running paces of the runner to be evaluated for the predetermined sections i based on Formula (1) shown below, and the recommended running pace calculation device calculates the recommended running pace for the runner to be evaluated based on Formula (2) shown below.

Corrected running pace for each predetermined section $i = F(P\max, Pi)$ (1)

$$\text{Recommended running pace} = \left(\sum_{i=1}^{n} Li \cdot F(P\max, Pi)\right) \bigg/ \sum_{i=1}^{n} Li \quad (2)$$

With the preferred configuration described above, with Pi denoting the running paces for the predetermined sections i, and Pmax denoting the fastest running pace, the correction device uses the correction function F(Pmax, Pi) shown in Formula (1) to correct the running paces Pi for the predetermined sections i, and calculates an average value of the corrected running paces F(Pmax, Pi) for the predetermined sections i as the recommended running pace for the runner to be evaluated, as shown in Formula (2). According to the findings made by the present inventors, when the running paces for the predetermined sections i are corrected with the preferable configuration described above to calculate the recommended running pace for the runner to be evaluated, the calculated recommended running pace is a recommended running pace that is appropriate for the runner to be evaluated.

In the first aspect of the present invention, it is preferred that the running pace acquisition device is provided in a mobile device carried by the runner to be evaluated, the correlation storage device, the correction device, and the recommended running pace calculation device are provided in a server that is electrically connected to the mobile device, the running paces of the runner to be evaluated for the predetermined sections acquired by the running pace acquisition device are transmitted from the mobile device to the server, and the recommended running pace for the runner to be evaluated calculated by the recommended running pace calculation device is transmitted from the server to the mobile device.

With the preferred configuration described above, the running pace acquisition device is provided in the mobile device carried by the runner to be evaluated (e.g., a smartphone or smartwatch, etc.), and the correlation storage device, the correction device, and the recommended running pace calculation device are provided in the server electrically connected to the mobile device. The acquired running paces of the runner to be evaluated for the predetermined sections are transmitted from the mobile device to the server, and the recommended running pace for the runner to be evaluated is transmitted from the server to the mobile device.

Accordingly, only by carrying a known mobile device, such as a smartwatch provided with the running pace acquisition device using a GPS function or the like, the runner to be evaluated can be informed of the recommended running pace for the runner easily. In addition, an operator that operates the server can acquire running paces of many runners to be evaluated for predetermined sections in a form of information. Therefore, the operator can use the acquired information for, for example, further improvement of a function of the system.

However, the first aspect of the present invention is not limited to the preferable configurations described above but can adopt a configuration in which the running pace acquisition device, the correlation storage device, the correction device, and the recommended running pace calculation device are all provided in the mobile device or a configuration in which all of them are provided in the server.

To solve the problem, the present invention also provides a recommended running pace calculation method comprising: a correlation storage step of storing a first correlation including correlations between running distances run by unspecified runners and fastest running paces of the unspecified runners; a running pace acquisition step of acquiring running paces for predetermined sections in a distance running run by a runner to be evaluated, the distance running having a predetermined length; a correction step of extracting a fastest running pace of the running paces of the runner to be evaluated for the predetermined sections acquired in the running pace acquisition step, and correcting the running paces of the runner to be evaluated for the predetermined sections acquired in the running pace acquisition step, based on the extracted fastest running pace and the first correlation stored in the correlation storage step; and a recommended running pace calculation step of calculating a recommended running pace in the distance running recommended to the runner to be evaluated based on the corrected running paces of the runner to be evaluated for the predetermined sections corrected in the correction step.

To solve the problem, the present invention provides, as a second aspect, a recommended running pace calculation system comprising: a correlation storage device in which a second correlation is stored, the second correlation being a correlation between running pace feature that is defined using an average running pace and a variation of running paces in a distance running having a predetermined length run by unspecified runners and recommended running pace in the distance running; a running pace feature calculation device configured to calculate a running pace feature that is defined using an average running pace and a variation of running paces in the distance running run by a runner to be evaluated; and a recommended running pace calculation device configured to calculate a recommended running pace in the distance running recommended to the runner to be evaluated, based on the running pace feature of the runner to be evaluated calculated by the running pace feature calculation device and the second correlation stored in the correlation storage device.

According to the second aspect of the present invention, the running pace feature calculation device calculates the running pace feature that is defined using the average running pace and the variation of running paces in the distance running having a predetermined length that is actually run by the runner to be evaluated. As the running pace feature, for example, a feature expressed as a linear sum of the average running pace and the variation of the running paces (standard deviation, mean square error, etc.) can be used. Then, the recommended running pace calculation device calculates the recommended running pace in the same distance running recommended to the runner to be evaluated, based on the calculated running pace feature of the runner to be evaluated and the second correlation (correlation between the running pace feature and the recommended running pace in the distance running) stored in the correlation storage device. According to the findings made by the present inventors, there is a relatively good correlation between the running pace feature defined using the average running pace and the variation of the running paces and the recommended running pace. Accordingly, the recommended running pace calculated by the recommended running pace calculation device is the recommended running pace appropriate to the runner to be evaluated.

As seen from the above, according to the second aspect of the present invention, a recommended running pace that is recommended to a runner to be evaluated for a distance running can be calculated based on the running paces in the same distance running (the average running pace and the variation of the running paces) that are acquired through the actual run of the runner to be evaluated.

The second correlation can be created by, for example, measuring running paces of unspecified runners for predetermined sections in a distance running having a predetermined length and calculating an average running pace and a variation of the running paces, in addition, measuring maximum oxygen consumptions (VO2max) of the same unspecified runners and calculating recommended running paces commensurate with abilities of the unspecified runners, and associating and organizing these correlations.

Specifically, in the second aspect of the present invention, it is preferred that the second correlation is created through statistical processing or machine learning using the running pace feature of the unspecified runners and the recommended running pace.

To solve the problem, the present invention also provides a recommended running pace calculation method comprising: a correlation storage step of storing a second correlation, the second correlation being a correlation between running pace feature that is defined using an average running pace and a variation of running paces in a distance running having a predetermined length run by unspecified runners and recommended running pace in the distance running; a running pace feature calculation step of calculating a running pace feature that is defined using an average running pace and a variation of running paces in the distance running run by a runner to be evaluated; and a recommended running pace calculation step of calculating a recommended running pace in the distance running recommended to the runner to be evaluated, based on the running pace feature of the runner to be evaluated calculated in the running pace feature calculation step and the second correlation stored in the correlation storage step.

Advantageous Effect of Invention

According to the present invention, a recommended running pace that is recommended to a runner to be evaluated for a distance running having a predetermined length can be calculated based on running paces in the same distance running that are acquired through an actual run of the runner to be evaluated.

DESCRIPTION OF EMBODIMENTS

Referring to the accompanying drawings as appropriate, a recommended running pace calculation system and a recommended running pace calculation method according to embodiments of the present invention will be described below.

First Embodiment

Figure 1A:
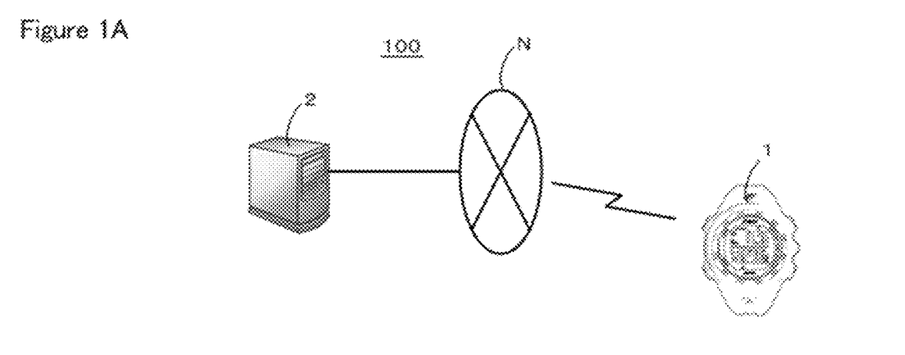
FIGS. 1A and 1B are diagrams illustrating a schematic configuration of a recommended running pace calculation system according to a first embodiment of the present invention.
Figure 1B:
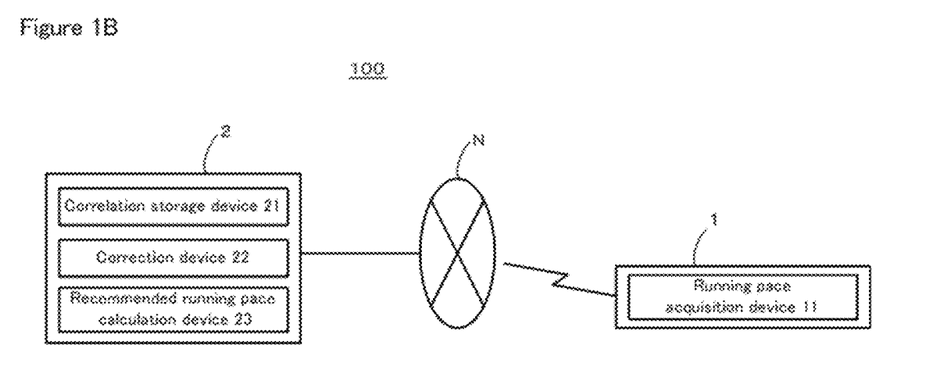

FIGS. 1A and 1B are diagrams illustrating a schematic configuration of a recommended running pace calculation system according to a first embodiment of the present invention. FIG. 1A is a schematic diagram illustrating a system configuration, and FIG. 1B is a block diagram of the system configuration.

As illustrated in FIGS. 1A and 1B, a recommended running pace calculation system 100 according to the present embodiment includes a correlation storage device 21, a running pace acquisition device 11, a correction device 22, and a recommended running pace calculation device 23.

In the present embodiment, the running pace acquisition device 11 is provided in a mobile device 1 carried by a runner to be evaluated (not illustrated) (in the example illustrated in FIGS. 1A and 1B, a smartwatch worn by the runner to be evaluated). Specifically, a GPS function or the like provided in the mobile device 1 (smartwatch) functions as the running pace acquisition device 11.

In the present embodiment, the correlation storage device 21, the correction device 22, and the recommended running pace calculation device 23 are provided in a server 2 that is electrically connected to the mobile device 1 through a telecommunications line N such as the Internet. Specifically, the correlation storage device 21 is constituted by a memory such as a ROM and RAM, a hard disk, or the like provided in the server 2. The correction device 22 and the recommended running pace calculation device 23 are implemented in a form of programs installed in the server 2 for carrying out functions of the devices.

The present embodiment is described about a configuration in which the running pace acquisition device 11 is provided in the mobile device 1, and the correlation storage device 21, the correction device 22, and the recommended running pace calculation device 23 are provided in the server 2, by way of example as described above, but the present invention is not limited to this configuration, and a configuration in which the running pace acquisition device 11, the correlation storage device 21, the correction device 22, and the recommended running pace calculation device 23 are all provided in the mobile device 1 or a configuration in which all of them are provided in the server 2 can be adopted.

A recommended running pace calculation method using the recommended running pace calculation system 100 with the above-described configuration will be described below.

Figure 2:
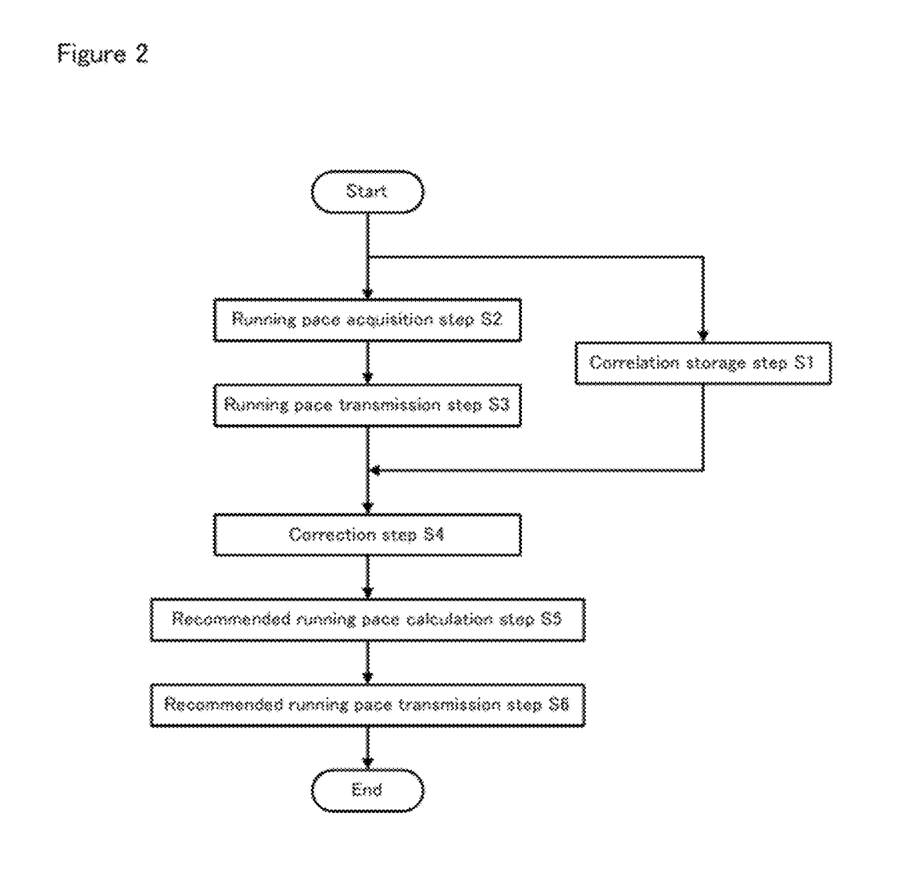
FIG. 2 is a flow diagram illustrating a schematic procedure of a recommended running pace calculation method according to the first embodiment of the present invention.

FIG. 2 is a flow diagram illustrating a schematic procedure of a recommended running pace calculation method according to the first embodiment of the present invention.

As illustrated in FIG. 2, the recommended running pace calculation method according to the present embodiment includes a correlation storage step S1, a running pace acquisition step S2, a correction step S4, and a recommended running pace calculation step S5. Additionally, since the present embodiment has, as described above, the configuration in which the running pace acquisition device 11 is provided in the mobile device 1, and the correlation storage device 21, the correction device 22, and the recommended running pace calculation device 23 are provided in the server 2 (i.e., an apparatus provided with the running pace acquisition device 11 is separate from an apparatus provided with the correlation storage device 21, the correction device 22, and the recommended running pace calculation device 23), a running pace transmission step S3 and a recommended running pace transmission step S6 are further included.

The steps S1 to S6 will be described below one by one.

[Correlation Storage Step S1]

In the correlation storage step S1, a first correlation, which includes correlations between running distances run by unspecified runners and their fastest running paces, is stored in the correlation storage device 21. The first correlation may be stored in the correlation storage device 21 permanently (e.g., in a case where the correlation storage device 21 is constituted by a ROM or a hard disk), or may be stored temporarily by externally inputting the first correlation into the server 2 when the recommended running pace calculation method according to the present embodiment is performed (e.g., in a case where the correlation storage device 21 is constituted by a RAM).

Figure 3:
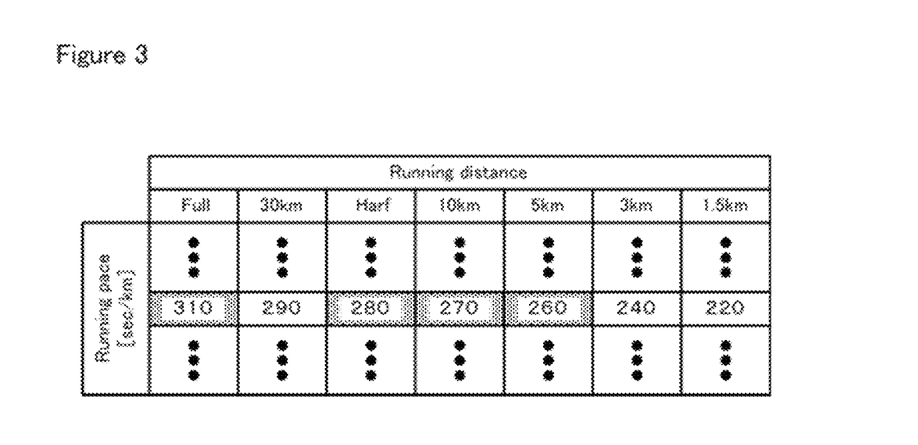
FIG. 3 is a diagram schematically illustrating an example of a first correlation.

FIG. 3 is a diagram schematically illustrating an example of the first correlation.

The first correlation can be created statistically by measuring running paces that are obtained by dividing times taken by unspecified runners to run various running distances at highest speeds by the running distances, and by associating and organizing correlations between the running distances and the running paces.

The first correlation illustrated in FIG. 3 shows correlations between running distances and fastest running paces, in a table form, such as those who can run 5 km at a fastest running pace of 260 sec/km can run 10 km at a fastest running pace of 270 sec/km, and those who can run a half marathon at a fastest running pace of 280 sec/km can run a full marathon at a fastest running pace of 310 sec/km. Note that the present invention is not limited to this; the first correlation can be expressed in a form of a function.

[Running Pace Acquisition Step S2]

In the running pace acquisition step S2, the running pace acquisition device 11 acquires running paces for predetermined sections in a distance running run by a runner to be evaluated, the distance running having a predetermined length. For example, in a case where the distance running having the predetermined length is a full marathon, running paces may be acquired for sections that include first four sections each having 10 km or first eight sections each having 5 km, and a remaining section having 2.195 km. For example, in a case where the distance running having the predetermined length is a half marathon, running paces may be acquired for sections that include first two sections each having 10 km or first four sections each having 5 km, and a remaining section having 1.0975 km.

[Running Pace Transmission Step S3]

In the running pace transmission step S3, the running paces of the runner to be evaluated for the predetermined sections acquired by the running pace acquisition device 11 is transmitted from the mobile device 1 to the server 2 over the telecommunications line N.

In a case where the running pace acquisition device 11, the correlation storage device 21, the correction device 22, and the recommended running pace calculation device 23 are all provided in the mobile device 1, the running pace transmission step S3 of transmitting the running paces from the mobile device 1 to the server 2 over the telecommunications line N is unnecessary.

[Correction Step S4]

In the correction step S4, the correction device 22 extracts a fastest running pace of the running paces of the runner to be evaluated for the predetermined sections, which have been acquired in the running pace acquisition step S2 and transmitted in the running pace transmission step S3. Then, based on the extracted fastest running pace and the first correlation stored in the correlation storage step S1, the correction device 22 corrects the running paces of the runner to be evaluated for the predetermined sections acquired in the running pace acquisition step S2. In the correction step S4 of the present embodiment, the first correlation is not used as it is, but a correction function that is created based on the first correlation is used for the correction.

The correction step S4 of the present embodiment will be described below more specifically.

In the correlation storage device 21 of the present embodiment, a correction function corresponding to the fastest running pace, which is created based on the first correlation, is stored. The correction function is specifically a function of fastest running pace and running pace for each predetermined section of a distance running as variables. The correction function may be created manually based on the first correlation and stored in the correlation storage device 21, or may be created automatically by the correction device 22 based on the first correlation and stored in the correlation storage device 21. As with the first correlation, the correction function may be stored in the correlation storage device 21 permanently, or may be stored temporarily by externally inputting the correction function into the server 2 when the recommended running pace calculation method according to the present embodiment is performed.

How to create the correction function will be described below specifically.

Figure 4A:
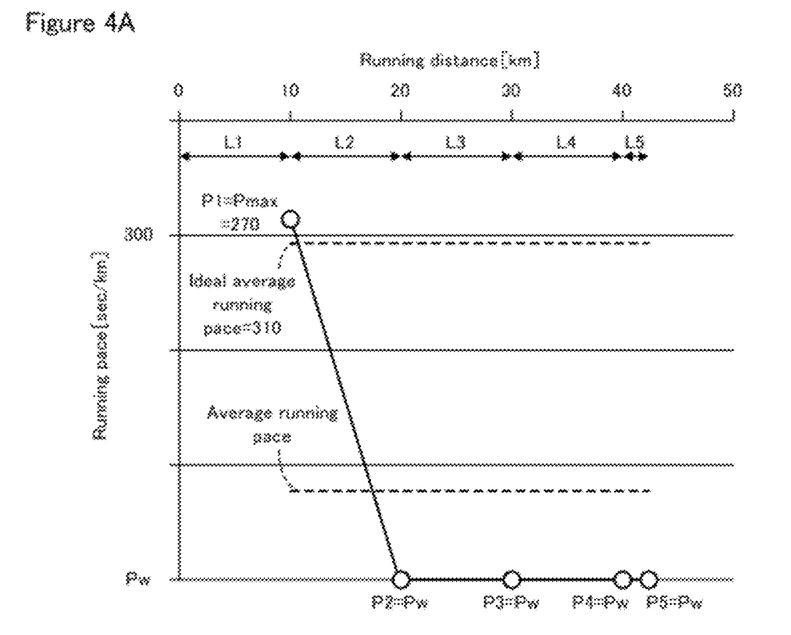
FIGS. 4A and 4B are explanatory diagrams used for describing an example of how to create a correction function.
Figure 4B:
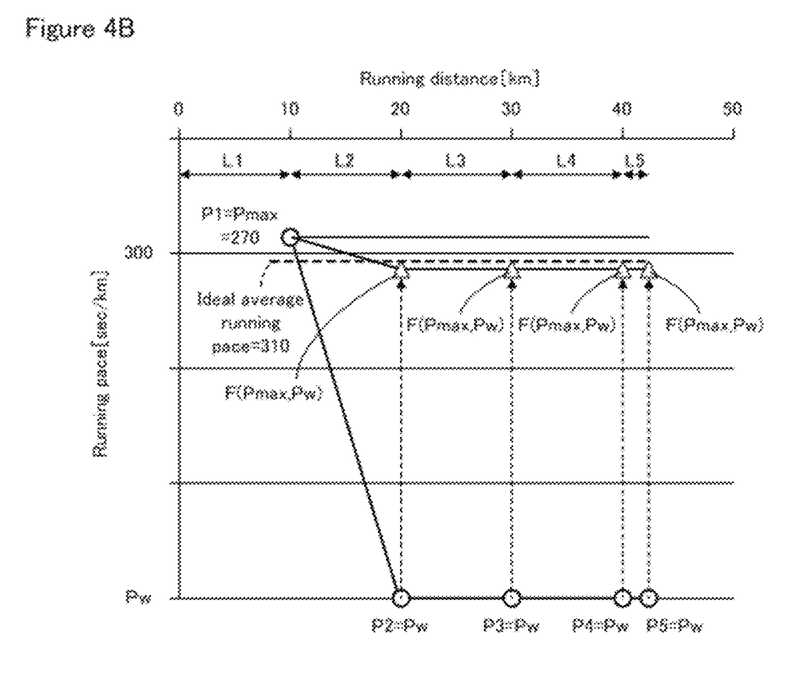

FIGS. 4A and 4B are explanatory diagrams used for describing examples of how to create the correction function. In FIGS. 4A and 4B, their horizontal axes indicate running distance and their vertical axes indicate running pace. On the vertical axes, a lower position indicates a greater value. In FIGS. 4A and 4B, Li denotes a length of each predetermined section i (i=1 to 5) in a distance running (a full marathon in the examples illustrated in FIGS. 4A and 4B). Pi denotes a running pace of each predetermined section i. Pmax denotes a fastest running pace of the running paces Pi of the predetermined sections i. Pw denotes a running pace in walking. F(Pmax, Pi) denotes the correction function. In the examples illustrated in FIGS. 4A and 4B, L1=L2=L3=L4=10 km, and L5=2.195 km.

In creating the correction function, first, as illustrated in FIG. 4A, the first correlation is used to calculate an ideal average running pace in a distance running, on the assumption that a given section is run at the fastest running pace Pmax and remaining sections are walked at a running pace Pw, as a first step. In the example illustrated in FIG. 4A, a case where a first section 1 (a section having a distance L1) is run at the fastest running pace Pmax (i.e., P1=Pmax), remaining sections 2 to 5 (sections having distances L2 to L5) are walked (i.e., P2=P3=P4=P5=Pw) is assumed, as marked as "O" in FIG. 4A. An average running pace at this time is a large value depending on the running pace Pw in walking. Then, for example, in a case where a running pace P1 of the section 1 having a running distance of 10 km is P1=Pmax=270 sec/km, a fastest running pace of a full marathon of 310 sec/km corresponds from the first correlation illustrated in FIG. 3, and thus the ideal average running pace is 310 sec/km, which is a value less than the average running pace.

Next, as a second step, in a case where the running paces Pi for the predetermined sections i in the distance running with the assumption are corrected as shown in Formula (1) shown below based on the correction function F(Pmax, Pi) corresponding to the fastest running pace Pmax (more specifically, a function of fastest running pace Pmax and running pace Pi of each predetermined section i as variables), the correction function F(Pmax, Pi) is determined such that the ideal average running pace calculated in the first step is obtained.

$$\text{Corrected running pace for each predetermined section } i = F(P\text{max}, Pi) \quad (1)$$

where F(Pmax, Pmax)=Pmax

Specifically, in the examples illustrated in FIGS. 4A and 4B, the running pace P1 of the section 1 is P1=Pmax, and running paces P2 to P5 for the sections 2 to 5 satisfy P2=P3=P4=P5=Pw, corrected running paces of the predetermined sections are F(Pmax, Pmax)=Pmax for the section 1 and F(Pmax, Pw) for the sections 2 to 5, as illustrated in FIG. 4B.

Accordingly, averaging the corrected running paces of the predetermined sections i satisfies the following Formula (2)'.

$$\text{Corrected average running pace} = \left(\sum_{i=1}^{5} Li \cdot F(P\text{max}, Pi)\right) \bigg/ \sum_{i=1}^{5} Li - \quad (2)'$$

$$(10 \cdot P\text{max} + 32.195 \cdot F(P\text{max}, Pw))/42.195$$

In the second step, the correction function F(Pmax, Pw) is determined such that this corrected average running pace is equal to the ideal average running pace calculated in the first step (310 sec/km in the examples illustrated in FIGS. 4A and 4B).

Then, for example, by performing the first step and second step described above repeatedly with the running pace Pw in walking being fixed and a value of the fastest running pace Pmax being changed, the correction function F(Pmax, Pi) can be created. Note that the correction function F(Pmax, Pi) may be either of a linear function or a nonlinear function as long as the correction function makes the corrected average running pace expressed by the above-described Formula (2)' equal to the ideal average running pace.

Figure 5A:
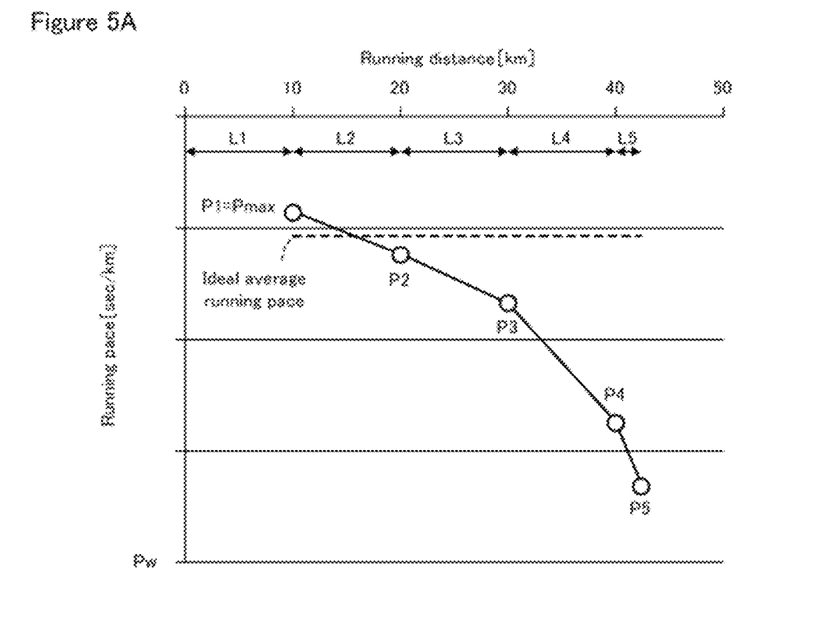
FIGS. 5A and 5B are explanatory diagrams used for describing a correction step S4 and a recommended running pace calculation step S5 illustrated in FIG. 2.
Figure 5B:
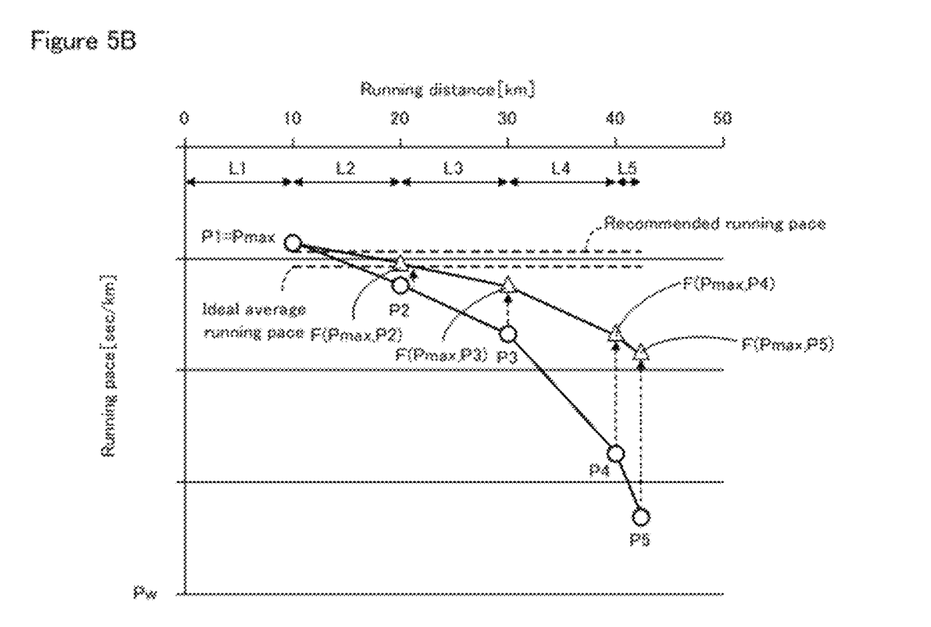

FIGS. 5A and 5B are explanatory diagrams used for describing the correction step S4 and the recommended running pace calculation step S5. In FIGS. 5A and 5B, their horizontal axes indicate running distance and their vertical axes indicate running pace. On the vertical axes, a lower position indicates a greater value.

In the correction step S4 of the present embodiment, the correction device 22 corrects, based on the extracted fastest running pace Pmax of the runner to be evaluated (P1=Pmax in the example illustrated in FIG. 5A) and the correction function F(Pmax, Pi) created in the above-described manner, the running paces Pi of the runner to be evaluated for the predetermined sections (i=1 to 5 in the example illustrated in FIG. 5A), as with Formula (1) shown above.

That is, with Li denoting lengths of predetermined sections i (i=1 to n, n=5 in the example illustrated in FIG. 5A) in the distance running run by the runner to be evaluated, Pi denoting running paces for the predetermined sections i, and Pmax denoting a fastest running pace of the running paces Pi for the predetermined sections i, the correction device 22 uses the created correction function F(Pmax, Pi) to correct the running paces Pi of the runner to be evaluated for the predetermined sections i based on Formula (1) shown below. In the example illustrated in FIG. 5A, although the running pace P1 remains P1 (Pmax) since the running pace P1 is equal to the fastest running pace Pmax, the running pace P2 is corrected to F(Pmax, P2), the running pace P3 is corrected to F(Pmax, P3), the running pace P4 is corrected to F(Pmax, P4), and the running pace P5 is corrected to F(Pmax, P5), as illustrated in FIG. 5B.

$$\text{Corrected running pace for each predetermined section } i = F(P\text{max}, Pi) \quad (1)$$

where F(Pmax, Pmax)=Pmax

[Recommended Running Pace Calculation Step S5]

In the recommended running pace calculation step S5, the recommended running pace calculation device 23 calculates a recommended running pace in a distance running recommended to the runner to be evaluated, based on the corrected running paces F(Pmax, Pi) of the runner to be evaluated for the predetermined sections corrected in the correction step S4. Specifically, the recommended running pace calculation device 23 calculates the recommended running pace for the runner to be evaluated based on Formula (2) shown below.

$$\text{Recommended running pace} = \left(\sum_{i=1}^{n} Li \cdot F(P\text{max}, Pi)\right) \bigg/ \sum_{i=1}^{n} Li \quad (2)$$

As illustrated in FIG. 5B, the calculated recommended running pace has a value that is less than the ideal average running pace determined from the first correlation illustrated in FIG. 3.

[Recommended Running Pace Transmission Step S6]

In the recommended running pace transmission step S6, the recommended running pace for the runner to be evaluated calculated by the recommended running pace calculation device 23 is transmitted from the server 2 to the mobile device 1 over the telecommunications line N.

In a case where the running pace acquisition device 11, the correlation storage device 21, the correction device 22, and the recommended running pace calculation device 23 are all provided in the server 2, the recommended running pace transmission step S6 of transmitting the recommended running pace from the server 2 to the mobile device 1 over the telecommunications line N is unnecessary.

By the recommended running pace calculation system 100 according to the present embodiment described above and the recommended running pace calculation method using the recommended running pace calculation system 100, in the running pace acquisition step S2, the running pace acquisition device 11 acquires running paces for predetermined sections i in a distance running having a predetermined length that is actually run by a runner to be evaluated. Then, in the correction step S4, the correction device 22 extracts a fastest running pace Pmax of the running paces of the runner to be evaluated for the predetermined sections, and based on the extracted fastest running pace Pmax and the first correlation stored in the correlation storage device 21 in the correlation storage step S1, the correction device 22 corrects the running paces of the runner to be evaluated for the predetermined sections i. The corrected running paces F(Pmax, Pi) for the predetermined sections i are running paces for the predetermined sections i that are commensurate with the fastest running pace Pmax of the runner to be evaluated, in other words, an intrinsic ability of the runner to be evaluated. Then, in the recommended running pace calculation step S5, the recommended running pace calculation device 23 calculates, based on the corrected running paces of the runner to be evaluated for the predetermined sections i, a recommended running pace in the same distance running recommended to the runner to be evaluated (in the present embodiment, an average value of the corrected running paces for the predetermined sections i). According to the findings made by the present inventors, the calculated recommended running pace is a recommended running pace appropriate to the runner to be evaluated.

An example of a test for verifying appropriateness of the recommended running pace calculated by the recommended running pace calculation method according to the present embodiment will be described below.

In the test, a runner to be evaluated actually run 12 races of full marathons, running paces of predetermined sections were acquired, and based on the running paces, a recommended running pace was calculated. In addition, the same runner to be evaluated was subjected to measurement of anaerobic threshold (AT) pace several days before each race, and from results of the measurement, a predicted running pace of a full marathon was calculated.

Figure 6:
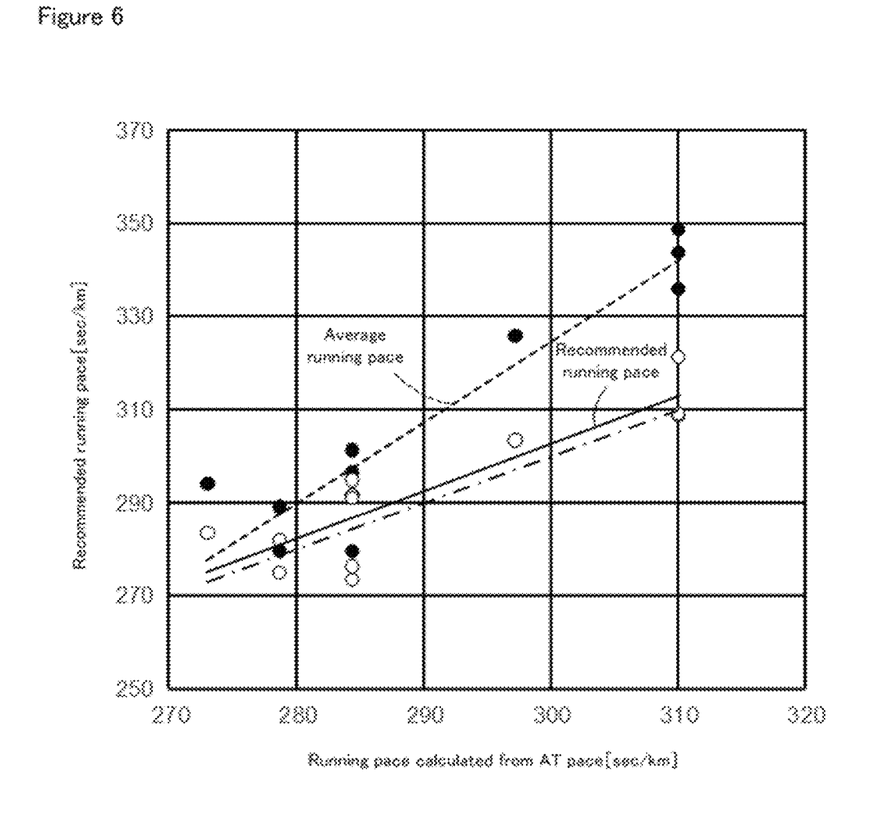
FIG. 6 illustrates results of a test for verifying appropriateness of a recommended running pace calculated by the recommended running pace calculation method according to the first embodiment of the present invention.

FIG. 6 illustrates results of the test. In FIG. 6, its horizontal axis indicates the running pace calculated (predicted) from the AT pace, and its vertical axis indicates the recommended running pace calculated by the recommended running pace calculation method according to the present embodiment. FIG. 6 also illustrates an average running pace of actual runs of the full marathons (data items marked as "•", and their regression line is illustrated as a broken line in FIG. 6). A dash-dot line illustrates cases at which a value of the horizontal axis matches a value of the vertical axis.

As understood from FIG. 6, the recommended running pace calculated by the recommended running pace calculation method according to the present embodiment (data items marked as "○", and their regression line is illustrated as a solid line in FIG. 6) relatively well matches the running pace calculated from the AT pace, and thus it can be said that the recommended running pace calculated by the recommended running pace calculation method according to the present embodiment is appropriate.

Second Embodiment

Figure 7A:
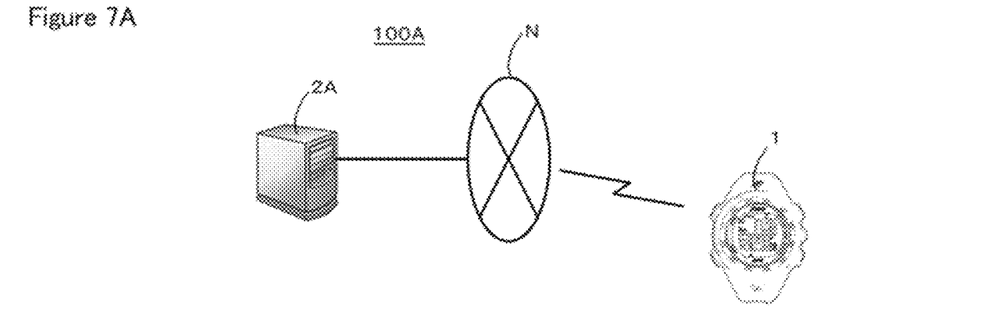
FIGS. 7A and 7B are diagrams illustrating a schematic configuration of a recommended running pace calculation system according to a second embodiment of the present invention.
Figure 7B:
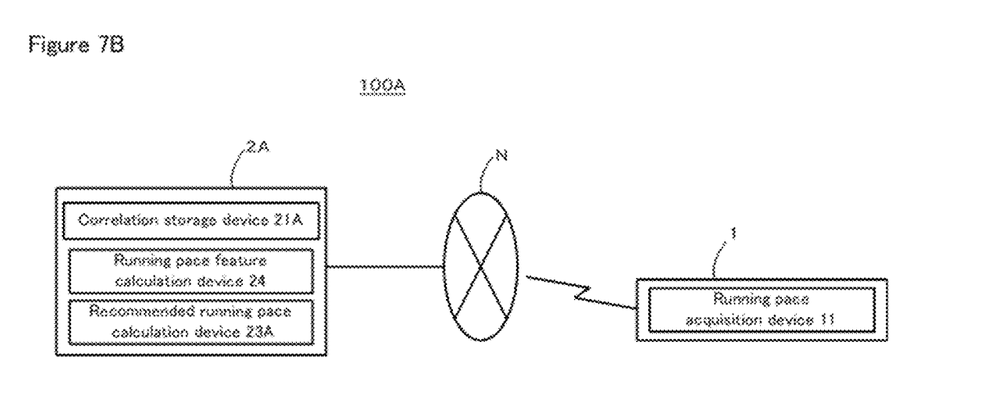

FIGS. 7A and 7B are diagrams illustrating a schematic configuration of a recommended running pace calculation system according to a second embodiment of the present invention. FIG. 7A is a schematic diagram illustrating a system configuration, and FIG. 7B is a block diagram of the system configuration.

As illustrated in FIGS. 7A and 7B, a recommended running pace calculation system 100A according to the present embodiment includes a correlation storage device 21A, a running pace acquisition device 11, a running pace feature calculation device 24, and a recommended running pace calculation device 23A.

Points of difference from the recommended running pace calculation system 100 according to the first embodiment will be mainly described below; constituent components having the same functions will be denoted by the same reference characters, and description thereof will be omitted as appropriate.

In the present embodiment, the running pace acquisition device 11 is still provided in a mobile device 1 carried by a runner to be evaluated (not illustrated) (in the example illustrated in FIGS. 7A and 7B, a smartwatch worn by the runner to be evaluated). Specifically, a GPS function or the like provided in the mobile device 1 (smartwatch) functions as the running pace acquisition device 11.

In the present embodiment, the correlation storage device 21A, the running pace feature calculation device 24, and the recommended running pace calculation device 23A are provided in a server 2A that is electrically connected to the mobile device 1 through a telecommunications line N such as the Internet. Specifically, the correlation storage device 21A is constituted by a memory such as a ROM and RAM, a hard disk, or the like provided in the server 2A. The running pace feature calculation device 24 and the recommended running pace calculation device 23A are implemented in a form of programs installed in the server 2A for carrying out functions of the devices.

The present embodiment is described about a configuration in which the running pace acquisition device 11 is provided in the mobile device 1, and the correlation storage device 21A, the running pace feature calculation device 24, and the recommended running pace calculation device 23A are provided in the server 2, by way of example as described above, but the present invention is not limited to this configuration, and a configuration in which the running pace acquisition device 11, the correlation storage device 21A, the running pace feature calculation device 24, and the recommended running pace calculation device 23A are all provided in the mobile device 1 or a configuration in which all of them are provided in the server 2A can be adopted.

A recommended running pace calculation method using the recommended running pace calculation system 100A with the above-described configuration will be described below.

Figure 8:
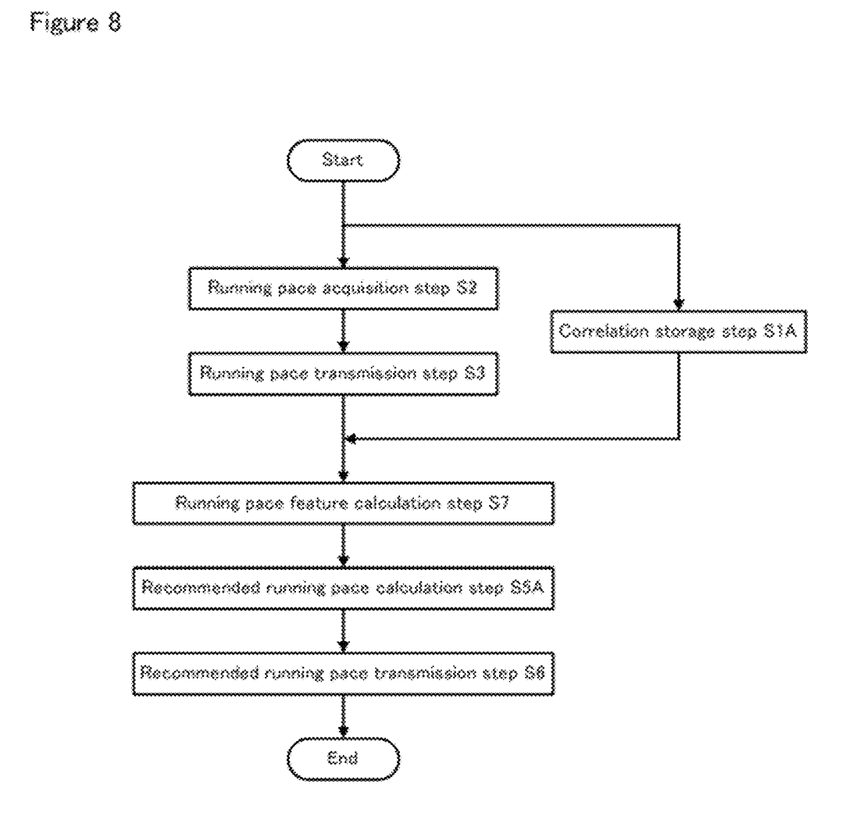
FIG. 8 is a flow diagram illustrating a schematic procedure of a recommended running pace calculation method according to the second embodiment of the present invention.

FIG. 8 is a flow diagram illustrating a schematic procedure of a recommended running pace calculation method according to the second embodiment of the present invention.

As illustrated in FIG. 8, the recommended running pace calculation method according to the present embodiment includes a correlation storage step S1A, a running pace acquisition step S2, a running pace feature calculation step S7, and a recommended running pace calculation step S5A. Additionally, since the present embodiment has, as described above, the configuration in which the running pace acquisition device 11 is provided in the mobile device 1, and the correlation storage device 21A, the running pace feature calculation device 24, and the recommended running pace calculation device 23A are provided in the server 2A (i.e., an apparatus provided with the running pace acquisition device 11 is separate from an apparatus provided with the correlation storage device 21A, the running pace feature calculation device 24, and the recommended running pace calculation device 23A), a running pace transmission step S3 and a recommended running pace transmission step S6 are further included.

The running pace acquisition step S2, the running pace transmission step S3, and the recommended running pace transmission step S6 are the same as those of the first embodiment, and thus description thereof will be omitted; the correlation storage step S1A, the running pace feature calculation step S7, and the recommended running pace calculation step S5A will be described below one by one.

[Correlation Storage Step S1A]

In the correlation storage step S1A, a second correlation, which is a correlation between running pace feature that is defined using an average running pace and a variation of running paces in a distance running having a predetermined length run by unspecified runners and recommended running pace in the distance running, is stored in the correlation storage device 21A. The second correlation may be stored in the correlation storage device 21A permanently (e.g., in a case where the correlation storage device 21A is constituted by a ROM or a hard disk), or may be stored temporarily by externally inputting the second correlation into the server 2A when the recommended running pace calculation method according to the present embodiment is performed (e.g., in a case where the correlation storage device 21A is constituted by a RAM).

As the running pace feature constituting the second correlation, for example, a linear sum of the average running pace and the variation of the running paces, a linear sum of the average running pace to the power of N (N≥2) and the variation of the running paces to the power of N (N≥2), the average running pace itself, and the variation of the running paces itself can be used. As the variation of the running paces, for example, a standard deviation, a mean square error, or the like of the running paces can be used. As the recommended running pace constituting the second correlation, for example, a recommended running pace calculated (predicted) from a maximum oxygen consumption (VO2max) measured or a recommended running pace calculated (predicted) from the AT pace measured can be used, or the fastest running pace calculated from the first correlation used in the first embodiment (see FIG. 3) can be used.

The second correlation can be created through statistical processing or machine learning such as a neural network using the running pace feature of unspecified runners and the recommended running pace.

Figure 9:
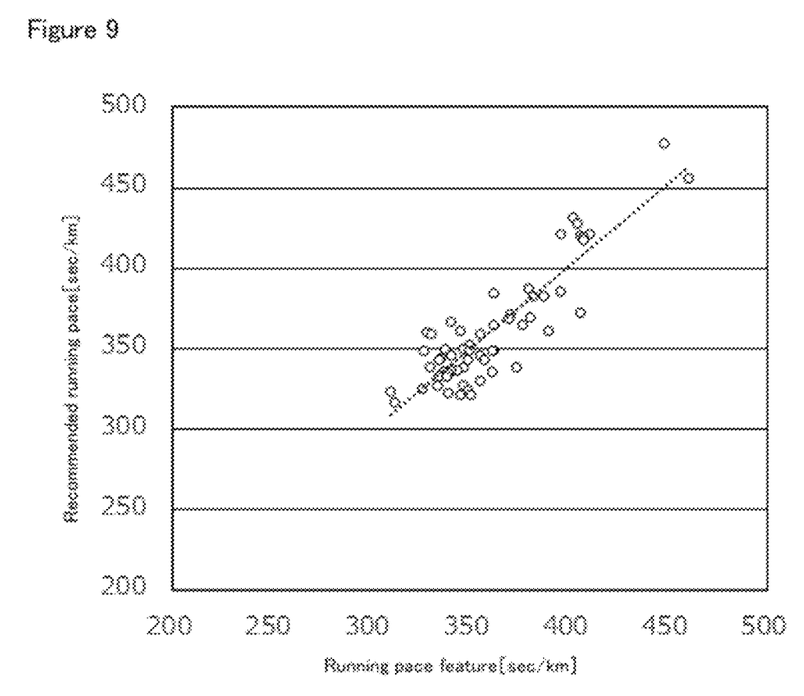
FIG. 9 is a graph illustrating an example of a second correlation created through statistical processing.

FIG. 9 is a graph illustrating an example of the second correlation created through the statistical processing. In FIG. 9, its horizontal axis indicates the running pace feature (a linear sum of an average running pace and a standard deviation of running paces in the example illustrated in FIG. 9), and its vertical axis indicates the recommended running pace. As illustrated in FIG. 9, there is a relatively good correlation between the running pace feature and the recommended running pace. The second correlation illustrated in FIG. 9 is represented in a form of a function (a regression line illustrated as a broken line) that is determined by regression calculation using multiple data points (points marked as "○" in FIG. 9), but the present invention is not limited to this, and the second correlation can be expressed in a form of a table.

[Running Pace Feature Calculation Step S7]

In the running pace feature calculation step S7, the running pace feature calculation device 24 calculates, based on the running paces of the runner to be evaluated for predetermined sections in the distance running acquired in the running pace acquisition step S2 and transmitted in the running pace transmission step S3, the average running pace and the variation of the running paces and calculates the running pace feature that is defined using the average running pace and the variation of the running paces.

[Recommended Running Pace Calculation Step S5A]

In the recommended running pace calculation step S5A, the recommended running pace calculation device 23A calculates a recommended running pace in the distance running recommended to the runner to be evaluated, based on the running pace feature of the runner to be evaluated calculated in the running pace feature calculation step S7 and the second correlation stored in the correlation storage step S1A. Specifically, for example, a value of the running pace feature calculated in the running pace feature calculation step S7 is input to the horizontal axis of FIG. 9, and a corresponding value of the vertical axis is calculated as the recommended running pace in the distance running recommended to the runner to be evaluated.

By the recommended running pace calculation system 100A according to the present embodiment described above and the recommended running pace calculation method using the recommended running pace calculation system 100A, in the running pace feature calculation step S7, the running pace feature calculation device 24 calculates a running pace feature that is defined using an average running pace and a variation of running paces in a distance running having a predetermined length that is actually run by a runner to be evaluated. Then, in the recommended running pace calculation step S5A, the recommended running pace calculation device 23A calculates a recommended running pace in the same distance running recommended to the runner to be evaluated, based on the calculated running pace feature of the runner to be evaluated and the second correlation (correlation between the running pace feature and the recommended running pace in the distance running) stored in the correlation storage device 21A in the correlation storage step S1A. According to the findings made by the present inventors, there is a relatively good correlation between the running pace feature defined using the average running pace and the variation of the running paces and the recommended running pace. Accordingly, the recommended running pace calculated in the recommended running pace calculation step S5A is a recommended running pace appropriate to the runner to be evaluated.

REFERENCE SIGNS LIST 100, 100A Recommended running pace calculation system
1 Mobile device
2, 2A Server
11 Running pace acquisition device 21, 21A Correlation storage device
22 Correction device
23, 23A Recommended running pace calculation device
24 Running pace feature calculation device
N Telecommunications line

The invention claimed is:

1. A recommended running pace calculation system comprising:
   a correlation storage device in which a first correlation is stored, the first correlation including statistical correlations between running distances run by unspecified runners and fastest running paces of the unspecified runners;
   a running pace acquisition device configured to acquire running paces for predetermined sections in a distance running run by a runner to be evaluated, the distance running having a predetermined length;
   a correction device configured to extract a fastest running pace of the running paces of the runner to be evaluated for the predetermined sections acquired by the running pace acquisition device, and to correct the running paces of the runner to be evaluated for the predetermined sections acquired by the running pace acquisition device, based on the extracted fastest running pace and the first correlation stored in the correlation storage device; and
   a recommended running pace calculation device configured to calculate a recommended running pace in the distance running recommended to the runner to be evaluated based on the corrected running paces of the runner to be evaluated for the predetermined sections corrected by the correction device, wherein
      the running pace acquisition device is provided in a mobile device carried by the runner to be evaluated,
      the correlation storage device, the correction device, and the recommended running pace calculation device are provided in a server that is electrically connected to the mobile device,
      the running paces of the runner to be evaluated for the predetermined sections acquired by the running pace acquisition device are transmitted from the mobile device to the server,
      the recommended running pace for the runner to be evaluated calculated by the recommended running pace calculation device is transmitted from the server to the mobile device,
      in the correlation storage device, a correction function corresponding to a fastest running pace created based on the first correlation, is stored,
      the correction device corrects the running paces of the runner to be evaluated for the predetermined sections based on the extracted fastest running pace of the runner to be evaluated and the correction function,
      with Li denoting lengths of predetermined sections i (i=1 to n) in the distance running run by the runner to be evaluated, Pi denoting running paces for the predetermined sections i, and Pmax denoting a fastest running pace of the running paces Pi for the predetermined sections i,
      the correction device corrects the running paces of the runner to be evaluated for the predetermined sections i based on Formula (1) shown below, and
      the recommended running pace calculation device calculates the recommended running pace for the runner to be evaluated based on Formula (2) shown below:

Corrected running pace for each predetermined section $i = F(Pmax, Pi)$ (1)

where $F(Pmax, Pmax) = Pmax$;

$$\text{Recommended running pace} = \left(\sum_{i=1}^{n} Li \cdot F(Pmax, Pi)\right) / \sum_{i=1}^{n} Li. \quad (2)$$

2. The recommended running pace calculation system according to claim 1, wherein the correction function is created by:
   a first step of calculating, using the first correlation, an ideal average running pace in the distance running, on an assumption that a given section is run at a fastest running pace and a remaining section is walked; and
   a second step of determining the correction function such that the ideal average running pace calculated in the first step is obtained in a case where the running paces for the predetermined sections in the distance running with the assumption are corrected based on the correction function corresponding to the fastest running pace.

3. The recommended running pace calculation system according to claim 1, wherein the correction function is expressed as a function of a fastest running pace and running pace for each predetermined section of the distance running as variables.

4. A recommended running pace calculation method for a system comprising a mobile device and a server electrically connected to the mobile device, the method comprising:
   a correlation storage step of, on the server, storing a first correlation including statistical correlations between running distances run by unspecified runners and fastest running paces of the unspecified runners;
   a running pace acquisition step of, on the mobile device carried by a runner to be evaluated, acquiring running paces for predetermined sections in a distance running run by the runner to be evaluated, the distance running having a predetermined length;
   a first transmitting step of transmitting, from the mobile device to the server, the running paces of the runner to be evaluated for the predetermined sections;
   a correction step of, on the server, extracting a fastest running pace of the running paces of the runner to be evaluated for the predetermined sections acquired in the running pace acquisition step, and correcting the running paces of the runner to be evaluated for the predetermined sections acquired in the running pace acquisition step, based on the extracted fastest running pace and the first correlation stored in the correlation storage step;
   a recommended running pace calculation step of, on the server, calculating a recommended running pace in the distance running recommended to the runner to be evaluated based on the corrected running paces of the runner to be evaluated for the predetermined sections corrected in the correction step; and
   a second transmitting step of transmitting, from the server to the mobile device, the recommended running pace for the runner to be evaluated,
   wherein:
      the method further comprises storing a correction function corresponding to a fastest running pace created based on the first correlation,
      the method further comprises correcting the running paces of the runner to be evaluated for the predetermined sections based on the extracted fastest running pace of the runner to be evaluated and the correction function, with Li denoting lengths of predetermined sections i (i=1 to n) in the distance running run by the runner to be evaluated, Pi denoting running paces for the predetermined sections i, and Pmax denoting a fastest running pace of the running paces Pi for the predetermined sections i, the method further comprises correcting the running paces of the runner to be evaluated for the predetermined sections i based on Formula (1) shown below, and the recommended running pace calculation device calculates the recommended running pace for the runner to be evaluated based on Formula (2) shown below:

$$\text{Corrected running pace for each predetermined section } i = F(P\text{max}, Pi) \tag{1}$$

where $F(P\text{max}, P\text{max}) = P\text{max}$;

$$\text{Recommended running pace} = \left(\sum_{i=1}^{n} Li \cdot F(P\text{max}, Pi)\right) \bigg/ \sum_{i=1}^{n} Li. \tag{2}$$

* * * * *